(12) United States Patent
Lair et al.

(10) Patent No.: US 11,911,192 B2
(45) Date of Patent: Feb. 27, 2024

(54) MEDICAL CABINET AND WASTE DISPOSAL CONTAINER SYSTEM

(71) Applicant: Post Medical, Inc., Alpharetta, GA (US)

(72) Inventors: Anthony Christopher Lair, Milton, GA (US); Matthew Dean Walker, Alpharetta, GA (US)

(73) Assignee: Post Medical, Inc., Alpharetta, GA (US)

( * ) Notice: Subject to any disclaimer, the term of this patent is extended or adjusted under 35 U.S.C. 154(b) by 0 days.

(21) Appl. No.: 17/867,821

(22) Filed: Jul. 19, 2022

(65) Prior Publication Data

US 2023/0026566 A1  Jan. 26, 2023

Related U.S. Application Data

(60) Provisional application No. 63/224,003, filed on Jul. 21, 2021.

(51) Int. Cl.
| | |
|---|---|
| *B65F 1/00* | (2006.01) |
| *A61B 50/36* | (2016.01) |
| *A61B 90/92* | (2016.01) |
| *B65F 1/14* | (2006.01) |
| *A61B 50/10* | (2016.01) |

(52) U.S. Cl.
CPC ............ *A61B 50/362* (2016.02); *A61B 90/92* (2016.02); *B65F 1/1431* (2013.01); *A61B 2050/105* (2016.02); *B65F 2210/148* (2013.01); *B65F 2250/112* (2013.01)

(58) Field of Classification Search
CPC ............ A61M 2205/583; A61M 5/008; A61M 5/002; A61M 5/3205; A47B 53/02; A47B 67/02; B65F 1/1431; B65F 2210/148; B65F 2250/112; A61B 50/36; A61B 2050/105
USPC .......................................... 206/366, 370, 365
See application file for complete search history.

(56) References Cited

U.S. PATENT DOCUMENTS

| | | | | |
|---|---|---|---|---|
| 5,240,108 | A * | 8/1993 | Tonna .................. | A61B 50/362 211/84 |
| 5,259,501 | A * | 11/1993 | Withers .............. | A61M 5/3205 206/370 |
| 5,385,105 | A * | 1/1995 | Withers, Jr. ............ | F23G 5/448 110/238 |
| 7,513,363 | B2 * | 4/2009 | Brown ................ | A61M 5/3205 312/211 |
| 7,694,811 | B2 | 4/2010 | Brown et al. | |
| 8,573,426 | B2 * | 11/2013 | Maness ................. | B09B 3/0075 206/370 |
| 8,610,535 | B2 | 12/2013 | Hui | |
| 10,417,847 | B1 | 9/2019 | Shoenfeld | |

(Continued)

OTHER PUBLICATIONS

Sharps Container Cabinets, https://www.postmedical.com/products/cabinets/, 16 pages, Apr. 22, 2022.

(Continued)

*Primary Examiner* — King M Chu
(74) *Attorney, Agent, or Firm* — Merchant & Gould P.C.

(57) ABSTRACT

A metal cabinet for housing medical waste disposal containers includes a locking mechanism for controlled access into the metal cabinet and a cut-out or window integrated into the metal cabinet for visualization of a portion of the medical waste disposal container(s) housed therein.

10 Claims, 7 Drawing Sheets

(56) References Cited

U.S. PATENT DOCUMENTS

| | | | | |
|---|---|---|---|---|
| 2009/0120820 A1* | 5/2009 | Iske | .................... | A61B 50/362 |
| | | | | 414/808 |
| 2014/0159552 A1* | 6/2014 | Bravo | .................... | H02G 3/086 |
| | | | | 312/198 |
| 2016/0148452 A1* | 5/2016 | Torquemada Jiménez | .................. | |
| | | | | B65D 43/00 |
| | | | | 206/1.5 |
| 2019/0144204 A1* | 5/2019 | Brenckle | ............... | B65F 1/1426 |
| | | | | 220/263 |

OTHER PUBLICATIONS

SharpSafety Wall Cabinet Locking for 5 Quart Sharps 85161H-1 Each, https://www.medonthego.com/SharpSafety-Wall-Cabinet-Locking-for-5-Quart-Sharps-85161H-1-Each_p_130354.html, 4 pages, Apr. 21, 2022.

* cited by examiner

MEDICAL CABINET AND WASTE DISPOSAL CONTAINER SYSTEM

REFERENCE TO RELATED APPLICATION

This application claims the benefit of U.S. Provisional Patent Application No. 63/224,003, filed on Jul. 21, 2021, the disclosure of which is incorporated herein by reference in its entirety.

FIELD OF THE INVENTION

The present disclosure relates generally to medical waste disposal containers for sharps and other medical waste, as well as to metal cabinets for housing these containers.

BACKGROUND OF THE INVENTION

Various cabinets and containers are used in the medical industry, for instance, to store medical waste, protect against injury due to sharps, and to prevent diversion and theft of medications. It would be beneficial to develop new containers, cabinets, and related systems that are more robust with increased traceability and reliability. Accordingly, it is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Consistent with aspects of this invention, a system is disclosed that comprises (i) a medical waste disposal container, typically constructed of a polymer or plastic material, and (ii) a metal cabinet configured to house the medical waste disposal container, and in some aspects, configured to house one, two, or more than two medical waste disposal container(s). The metal cabinet can comprise (a) a locking mechanism for controlled access into the metal cabinet, and (b) a cut-out in the metal cabinet for visualization of a portion of the medical waste disposal container disposed therein.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description.

DEFINITIONS

Herein, features of the subject matter are described such that, within particular aspects, a combination of different features can be envisioned. For each and every aspect and/or feature disclosed herein, all combinations that do not detrimentally affect the designs, articles, and systems described herein are contemplated with or without explicit description of the particular combination. Additionally, unless explicitly recited otherwise, any aspect and/or feature disclosed herein can be combined to describe inventive designs, articles, and systems consistent with the present invention.

In this disclosure, while a system is often described in terms of "comprising" various parts or components, the system also can "consist essentially of" or "consist of" the parts or components, unless stated otherwise.

The terms "a," "an," and "the" are intended to include plural alternatives, e.g., at least one, unless otherwise specified.

Although any methods and materials similar or equivalent to those described herein can be used in the practice or testing of the invention, the typical methods and materials are herein described.

DETAILED DESCRIPTION OF THE INVENTION

Metal cabinets for housing medical waste disposal containers formed from plastic materials are disclosed herein, as well as metal cabinet and medical waste disposal container systems. Cabinet to container feature and design coordination is essential for enhanced safety to prevent sharps deposits from falling outside of the container, over filling of waste, mis-identification of container and waste type, and unwanted access or diversion of dangerous waste products.

Figure 1:
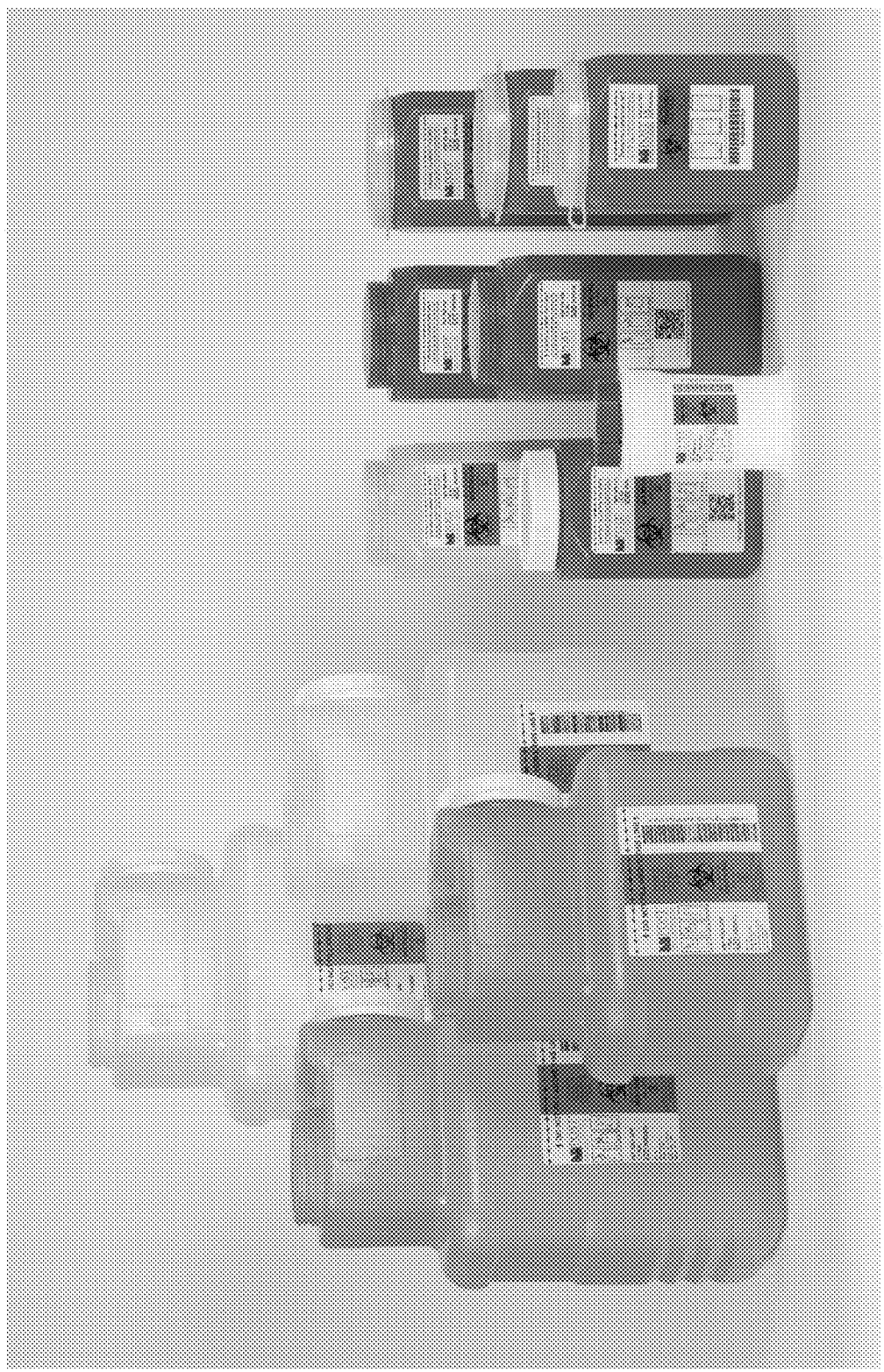
FIG. 1 is a color photograph of representative medical waste disposal containers formed from a suitable polymer or plastic material.

While not limited thereto, the cabinets disclosed herein can be configured to house a variety of medical waste disposal containers, and these waste disposal containers typically have a clear or translucent color or are opaque with a specific color based on the type of waste the container is designed to hold. Referring first to FIG. 1, representative medical waste disposal containers for medical waste or sharps are illustrated, where red containers are designed for sharps waste (e.g., needles and syringes), white containers are designed for pharmaceutical waste, yellow containers are designed for chemotherapy waste, and black containers are designed for CS waste (not shown in FIG. 1).

The medical waste disposal container can comprise or can be formed from any suitable polymer or plastic material, such as an ethylene-based polymer (e.g., a homopolymer or copolymer often referred to as high density polyethylene (HDPE) or linear low density polyethylene (LLDPE)), a propylene-based polymer (e.g., a homopolymer or copolymer), and the like. Combinations of more than one polymer can be used as the base material for the medical waste disposal container, and any suitable technique can be used to form the container, including blow molding, injection molding, and so forth. Pigment or colorant additives can be blended with the base polymer to yield the color options shown in FIG. 1. In order to enhance the end-users ability to confirm fill level and waste content, it can be beneficial to use pigments or colorants that are not opaque. A label can be present on the medical waste disposal container, often adhered onto the container body with an adhesive, although not limited thereto.

Further, each medical waste disposal container has a "fill line" that serves as an indicator of when the medical waste disposal container needs to be replaced, as shown in FIG. 1. The fill line can be present on the label adhered to the container in one aspect, while in another aspect, the fill line indicator can be present on the container body itself. The container's fill line marker can be used to confirm waste fill level by visualizing through the sides of translucent plastic materials or through the top of the container with opaque plastic materials. In a particular aspect of this invention, the medical waste disposal container can be configured to hold sharps such as blades, needles, or scalpels (the medical waste disposal container is a sharps waste disposal container).

Figure 2:
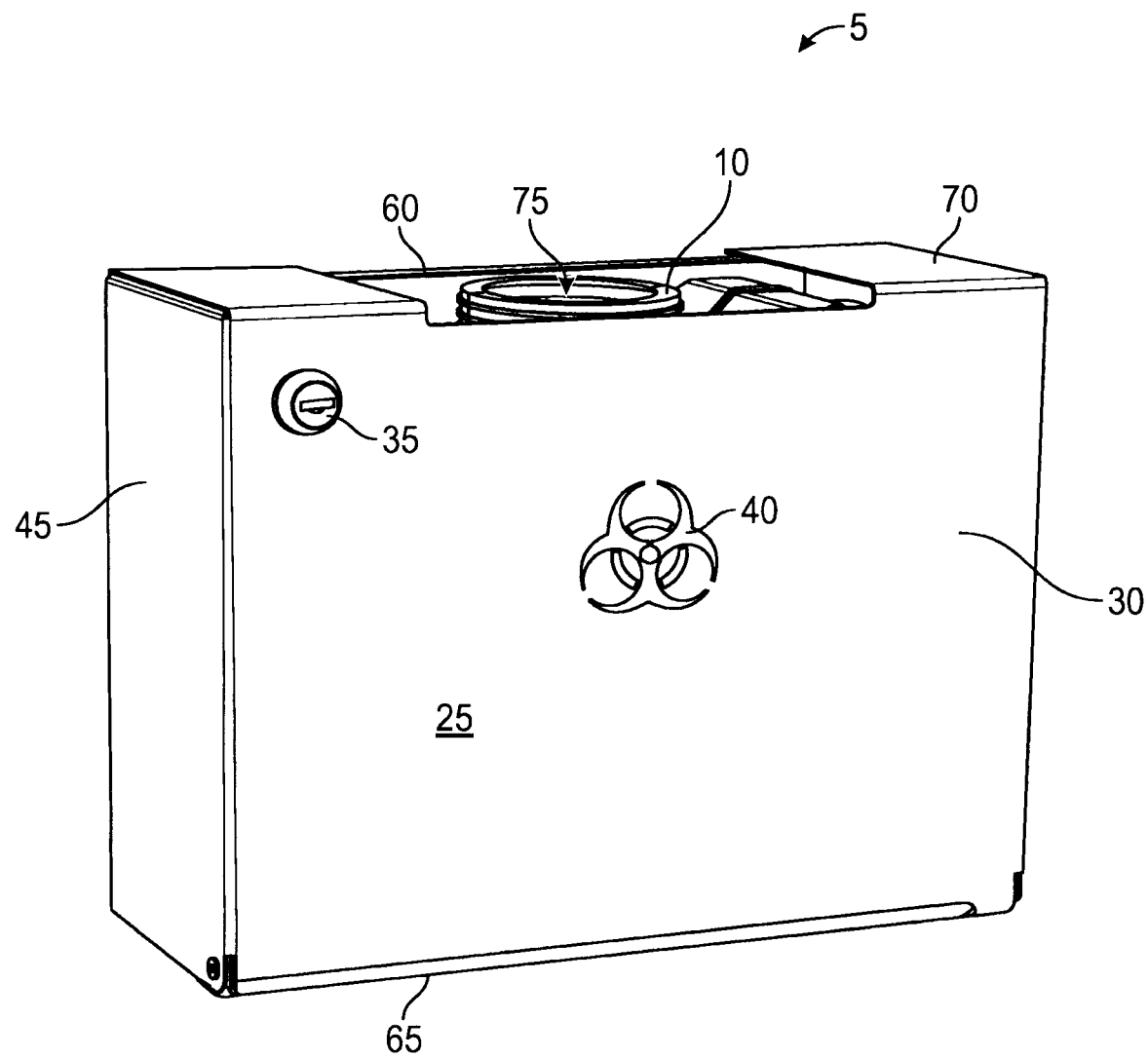
FIG. 2 is a front perspective view of a metal cabinet for housing one or more of the medical waste disposal containers shown in FIG. 1.
Figure 8:
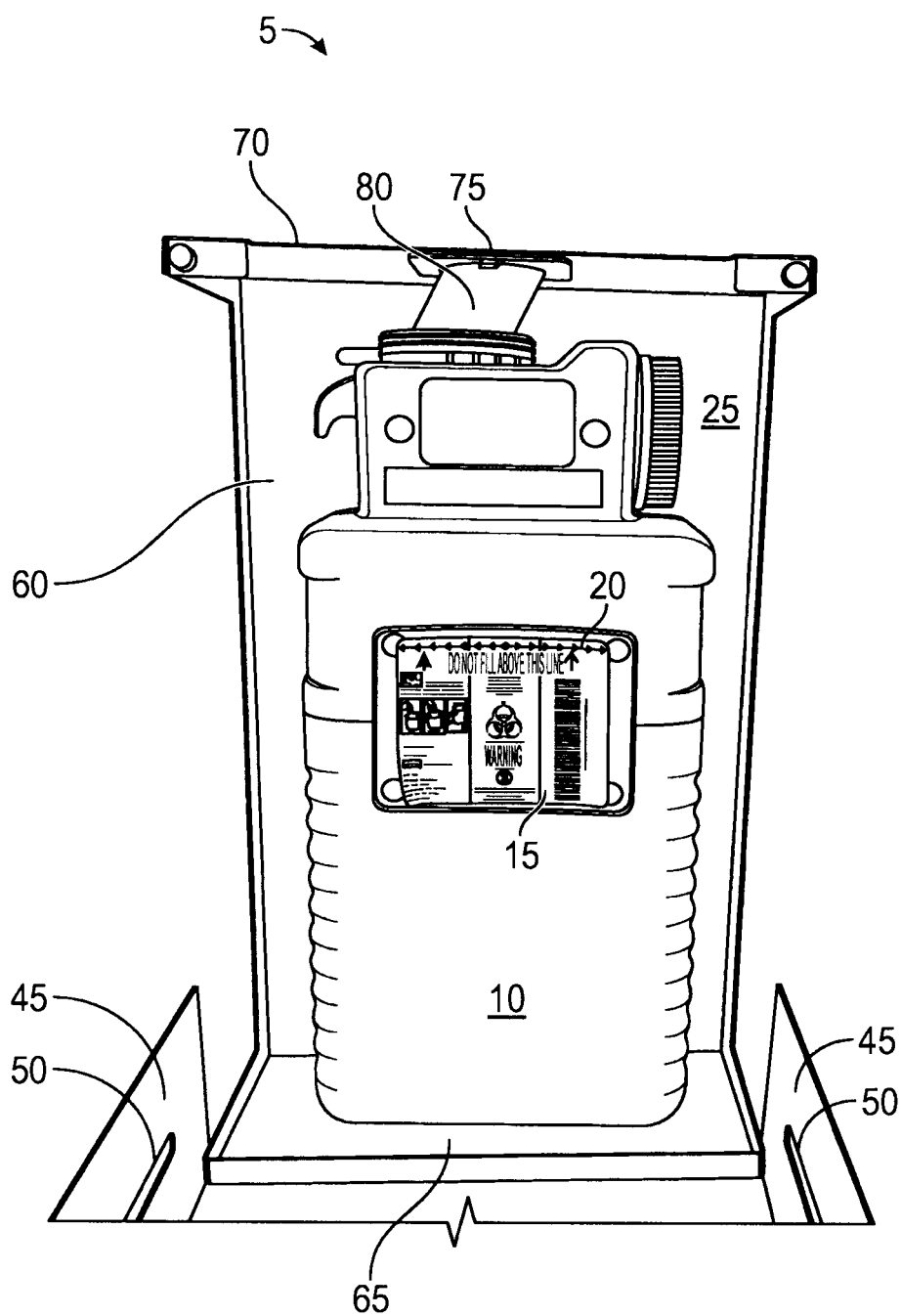
FIG. 8 is a perspective view of the metal cabinet shown in FIG. 3 in an opened position, with the metal cabinet housing a single medical waste disposal container shown in FIG. 1.

A system 5 of a metal cabinet 25 for housing (e.g., and securing) medical waste disposal container(s) 10 consistent with aspects of this invention is shown in FIG. 2. The metal cabinet 25 is an assembly which can include a front panel 30, side panels 45, back panel 60, bottom panel 65, and top panel 70. The front panel 30 can be positioned opposite the back panel 60. The side panels 45 can be parallel to each other and joined on opposite sides of the front panel 30 forming a U-shape. Additionally, the top panel 70 can be joined to a top edge of the front panel 30 and overlay a top surface of the back panel 60. The bottom panel 65 can be positioned opposite the top panel 70. The back panel 60 can be joined to the bottom panel 65 at a bottom surface. Optionally, the back panel 60 can alternatively have a second top panel, which the top panel 70 can overlay in a closed position. Additionally, the back panel 60 and bottom panel 65 can have a lip, best shown in FIG. 8, extending outward toward the interior of the cabinet 25. The lip can advantageously keep the medical waste disposal container 10 from sliding off the bottom panel 65 within the metal cabinet 25. The front panel 30 can include at least one cut-out 40 providing visibility of the interior of the metal cabinet and/or at least one locking mechanism 35 for holding the front panel 30 in the closed position and securing the medical waste disposal container 10 within the metal cabinet 25. The front panel 30, side panels 45, and top panel 70 are joined by any suitable connection means, such as a nut or bolt, to the bottom panel 65, and are pivotably moveable around the bottom panel 65 to an opened position (as shown in FIG. 8). The dimensions of the metal cabinet 25 can be any suitable dimension. For instance, the metal cabinet 25 can be square or rectangular in shape.

The metal cabinet 25 can be constructed of any suitable metal material, but the metal material from which the metal cabinet 25 is constructed is much stronger and more durable and secure than conventional transparent plastic cabinets. Typical metal materials can include various stainless steel materials, including 304, 316, 321, 347, 410S, 600, or 800 stainless steel, and the like. While not limited thereto, the thickness of the metal material used to construct the metal cabinet 25 often can be in the 16 to 18 gauge range (~1.2-1.6 mm thickness). Compared with plastic cabinets, stainless-steel materials or anti-microbial painted steel finishes can be utilized in environments where cross-contamination or touch contamination are a concern. Thus, the metal cabinet can be further configured to have anti-microbial or anti-bacterial properties, such as via the use of suitable coatings, paints, or finishes.

Not only does the metal cabinet 25 offer improved security compared to insecure transparent plastic cabinets for housing medical waste disposal containers 10, but even more so, these higher security metal cabinets 25 are more robust for protecting sharps waste from intrusion by addicts, prisoners, mental health patients, and the like, as compared to insecure plastic cabinets. This is particularly important for cabinet and container systems 5 that are utilized in prison hospitals and mental health facilities, where disposed sharps products (e.g., bladed waste, needles, scalpels) can be used as weapons, or where addicts are seeking residual medications from dispensed syringes. For metal cabinets 25 that house a sharps container 10, such as a FDA 510$k$ medical class 2 sharps container, robustness and high security are more important than for cabinets that merely house medical supplies or innocuous medical implements.

In an aspect, the metal cabinet 25 can be constructed of a weather-resistant stainless steel, optionally with all-weather locks, all-weather fasteners, etc., for use in public parks and any other public outdoor locations.

While not a requirement, and depending upon the particular public or private location, the metal cabinet 25 optionally can be designed with an opening 75 at the top of the metal cabinet 25—as shown in FIG. 2—where the opening 75 at the top of the metal cabinet 25 can be positioned above an opening of a medical waste disposal container 10. Thus, if desired, waste can be placed into a particular plastic container within the metal cabinet 25 without having to open the cabinet 25 and remove the medical waste disposal container 10 from the metal cabinet 25. The opening 75 can have a cross sectional area which prevents an individual from fitting objects such as hands through the opening, while still allowing sharps waste to be disposed through the opening 75. The cross-sectional area of the opening 75 can vary, for example, the cross-sectional area can range from 1 inch to 2 inches. Additionally, the shape of the opening 75 can be circular, elliptical, or other desired shapes.

Another beneficial feature of the metal cabinet 25, as compared to molded plastic-based cabinets, is a secure locking mechanism 35. FIG. 2 illustrates a typical lock/key entry into the metal cabinet 25, but the cabinets are not limited thereto. Any suitable locking mechanism 35 can be integrated into the metal cabinet 25, such as flat key cam locks, tubular cam locks, electronic cam locks, and the like, and thus cover a range from low to high security options. For instance, the metal cabinet 25 of FIG. 2 can contain two locks where two different keys are needed to gain entry into the metal cabinet 25. In an aspect, the front panel 30 can include a locking mechanism 35 for holding the front panel 30 in a closed position. The locking mechanism 35 can allow access to the medical waste disposal container 10 positioned within the metal cabinet 25 to be restricted by changing the locking mechanism 35 between a locked and unlocked position. When in a locked position, the front panel 30, side panels 45, and top panel 70 can be interconnected, such that the medical cabinet 25 is closed. The locking mechanism 35 can be placed at any suitable location on the front panel 30. As a non-limiting example, the locking mechanism 35 can be positioned at a corner between/adjacent the top panel 70 and one of the side panels 45 on the front panel 30. Alternatively, the locking mechanism can be located on other panels as desired.

Electronic lock technology allows for the facility in which the metal cabinet 25 is located to track access into the metal cabinet 25 (e.g., date, time, person), to schedule access or service relating to the cabinet 25 and its containers 10, and to control access to only qualified or authorized personnel. High security environments include prisons, mental health and drug treatment facilities, pain clinics, any public venue, hospitals, and long term care facilities. Such high security environments can require surveillance data collection and access control data recorded by electronic lock technology or by another suitable technique.

Various types of electronic lock systems can be used with the metal cabinet 25, such as a keypad affixed to the metal cabinet 25 and accessible from the outside of the metal cabinet 25 (the authorized personnel entering a password/pin number to open the metal cabinet 25 and optionally another password/pin number to identify the individual). Such a locking mechanism 35 would prevent unauthorized personnel from accessing the hazardous contents within the metal cabinet 25.

Alternatively, fingerprint recognition or related facial/iris recognition devices can be substituted for, or used in addition to, the electronic keypad entry. Also, the user can carry a RFID tag/badge or smart card, such that when within a particular range of or distance from the locking mechanism 35, the metal cabinet 25 can be automatically unlocked. The metal cabinets 25 disclosed herein are not limited by any particular locking mechanisms 35 or controlled access system/device used to gain entry into the cabinet 25.

The shape and size (or interior volume) of the metal cabinet 25 also is not particularly limited. In one aspect, the metal cabinet 25 can be in the shape of a rectangular prism, and the interior can be completely open (when no medical waste disposal containers 10 are present). In another aspect, the interior of the metal cabinet 25 can contain a shelf (one or more shelves) or a drawer (one or more drawers). If present, the shelf or drawer (or shelves or drawers) can be adjusted within the interior space of the metal cabinet 25.

Another important and advantageous feature of the metal cabinet 25 disclosed herein is illustrated in FIG. 2: one surface of the metal cabinet 25 has a laser cut-out 40 (or window). The laser cut-out 40 is a biohazard symbol for illustration purposes, but this is not limited to any particular symbol or design; any suitable logo, industry symbol, or non-descript symbol or design can be used. Moreover, more than one cut-out 40 can be integrated into the metal cabinet 25, and the cut-out(s) 40 can be positioned at any suitable location for viewing desirable information within the metal cabinet 25. The cut-out 40 can be provided as a small opening through the metal cabinet 25 or a see-through cover can additionally be positioned within or over the cut-out 40. As another feature, the cut-out 40 can illuminate the color of the medical waste disposal container 10 inside the metal cabinet 25. As a non-limiting example, if a red container 10 used for a sharps medical waste disposal container 10 is disposed within the metal cabinet 25, the cut-out 40 will make the red color visible indicating a sharps container 10 is within the metal cabinet 25. Thus, the "red" biohazard symbol signifies to a medical professional that the metal cabinet is purposed as a disposal site for sharps products.

The design also advantageously allows the metal cabinet 25 to be flexibly placed in any suitable location. The metal cabinet 25 can easily be mounted on a wall with well-known mounting mechanisms. As a benefit, when mounted on the wall, the fill line 20 can be more easily viewed through the cut-out 40. Alternatively, the metal cabinet 25 can be free-standing and placed on a surface, such as a table or counter. Beneficially, waste can be easily dropped into the opening 75 of a free-standing metal cabinet 25.

Figure 3:
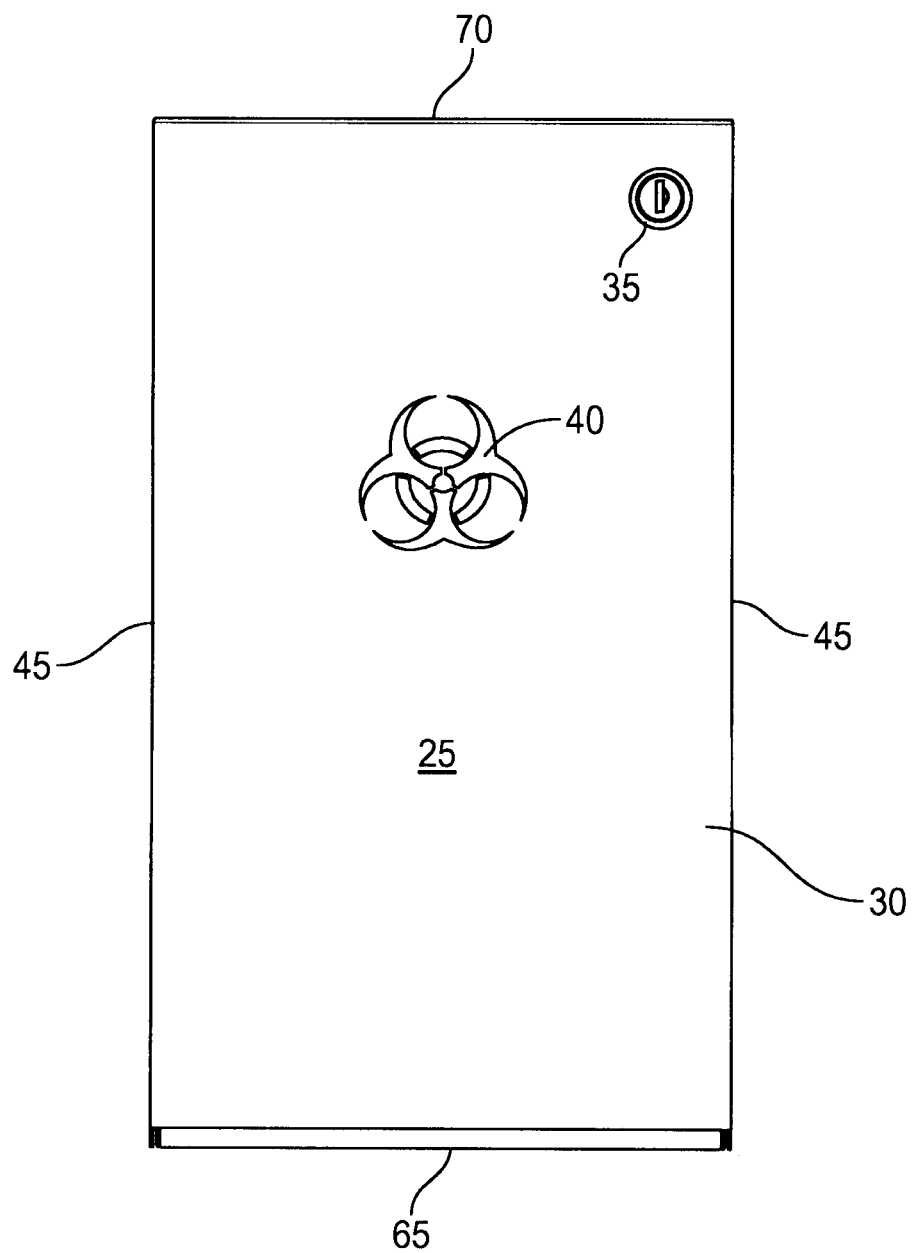
FIG. 3 is a front view of a metal cabinet for housing one or more of the medical waste disposal containers shown in FIG. 1.

FIG. 3 shows a front view of an alternative aspect of a rectangular metal cabinet 25 with the locking mechanism 35 and the laser cut-out 40. The locking mechanism 35 in this alternative aspect is positioned in the top right corner of the front panel 30. Additionally, the cut-out 40 is located in the center of the front panel 30 surface facing away from the interior of the metal cabinet 25.

Figure 4:
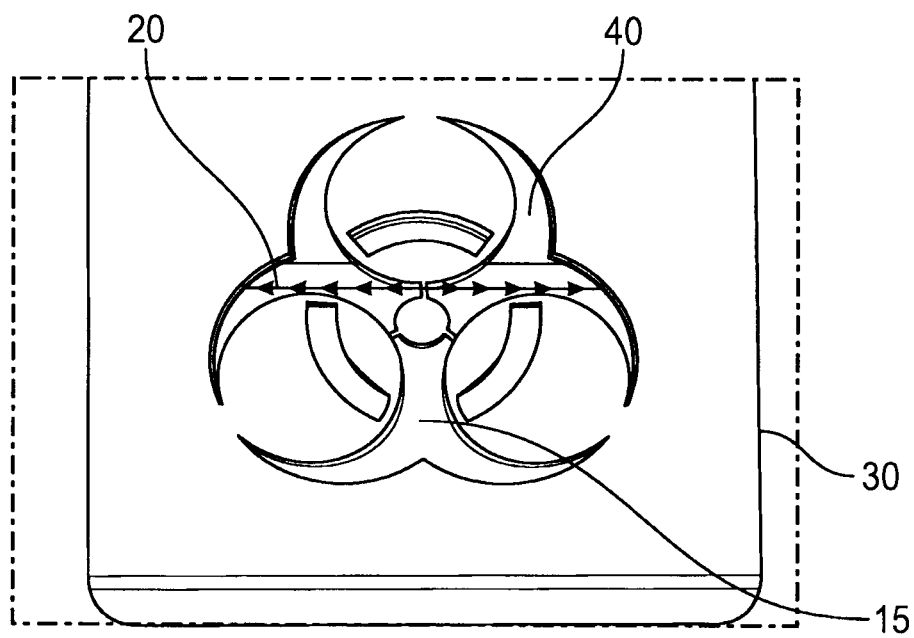
FIG. 4 is a close-up view of the metal cabinet of FIG. 2 to illustrate a laser cut-out symbol positioned in front of a label of the medical waste container disposed within the metal cabinet.

FIG. 4 is a close-up view of the laser cut-out 40, which shows the fill line 20 on the label 15 of the medical waste disposal container 10 housed within the metal cabinet 25. The fill line 20 can be aligned at a height of the cut-out 40 on the metal cabinet 25. Beneficially, the cut-out 40 in the metal cabinet 25 allows visualization inside the metal cabinet 25, such that the label 15 of the medical waste disposal container 10 can be viewed, a barcode on the label 15 of the medical waste disposal container 10 can be viewed or scanned (for container identifier/tracking information, lot number, etc.), a fill line 20 of the medical waste disposal container 10 (or fill line 20 on the label 15 on the medical waste disposal container 10) can be viewed as an indicator of when a medical waste disposal container 10 needs to be replaced, a color of the medical waste disposal container 10 can be determined (to confirm the type of waste container 10), and the like, as well as any combination of the above-described features (see also FIG. 8). These are merely representative examples of the type of information that can be obtained via the window or cut-out 40 present in the metal cabinet 25, and this invention is not limited solely to these representative examples.

Figure 5:
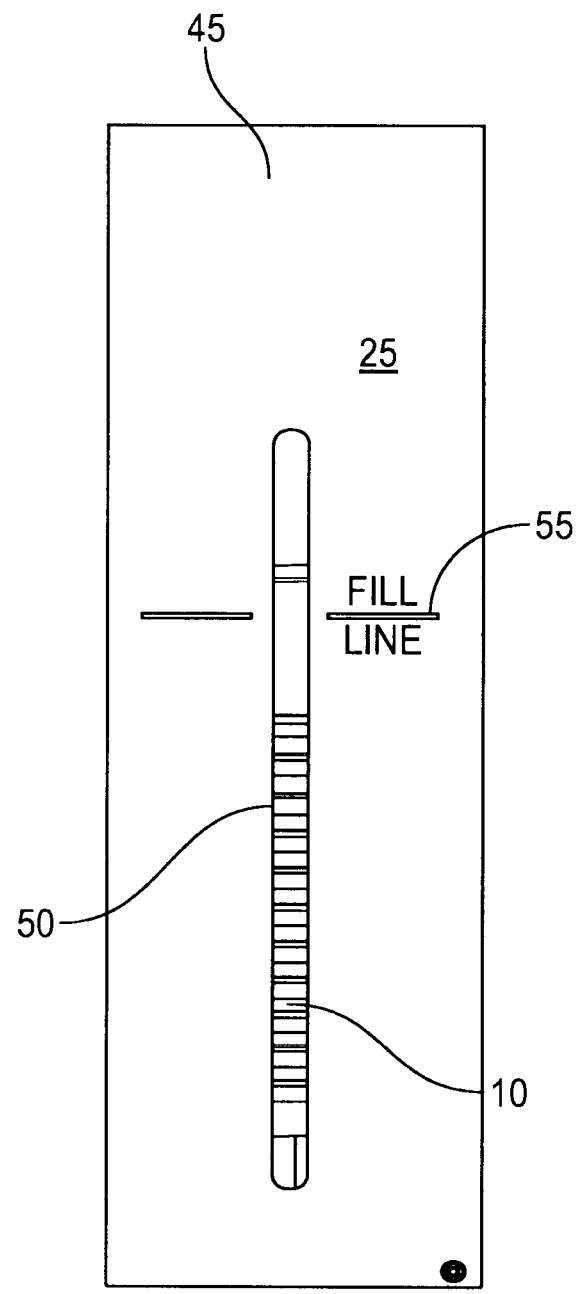
FIG. 5 is a side view of the metal cabinet shown in FIG. 3.

FIG. 5 is a side view of the metal cabinet 25 showing a side vent 50 on the metal cabinet 25 of FIG. 3. At least one side vent 50 can be disposed on each of the side panels 45. Each side vent 50 is an open portion or slit on a side panel 45 of the metal cabinet 25. Advantageously, the side vent 50 provides visibility to the medical waste disposal container 10 within the metal cabinet 25 when viewed from the sides of the metal cabinet 25. The side vent 50 has a width which allows visibility but restricts an individual's fingers or hand from being able to access contents within the metal cabinet 25 or the medical waste disposal container 10. A length of the side vent 50 extends longitudinally between the bottom panel 65 and the top panel 70. A fill line 55 is disposed on the side panel 45 indicating when the medical waste disposal container 10 has been filled with waste to a predetermined level. The fill line 55 is disposed adjacent to the side vent 50 and extends perpendicularly relative to length of the side vent 50. Additionally, the fill line 55 is aligned at the same position on the side panel 45 as the fill line 20 on the label 15 of the medical waste disposal container 10 within the cabinet as shown FIG. 4. When waste is dropped into the container 10 and the waste reaches the fill line 55, a user can see the level of waste within the container 10 through the side vent 50 and the fill line 55 indicates the container should be replaced (and this can be enhanced with a selection of a non-opaque colorant for the plastic container). Advantageously, the fill line 55 of side vent 50 can indicate, from outside the cabinet 25, that a medical waste disposal container 10 requires replacement by showing when the same predetermined level of waste has filled the container 10 as indicated by the fill line 20 of the label 15.

Figure 6:
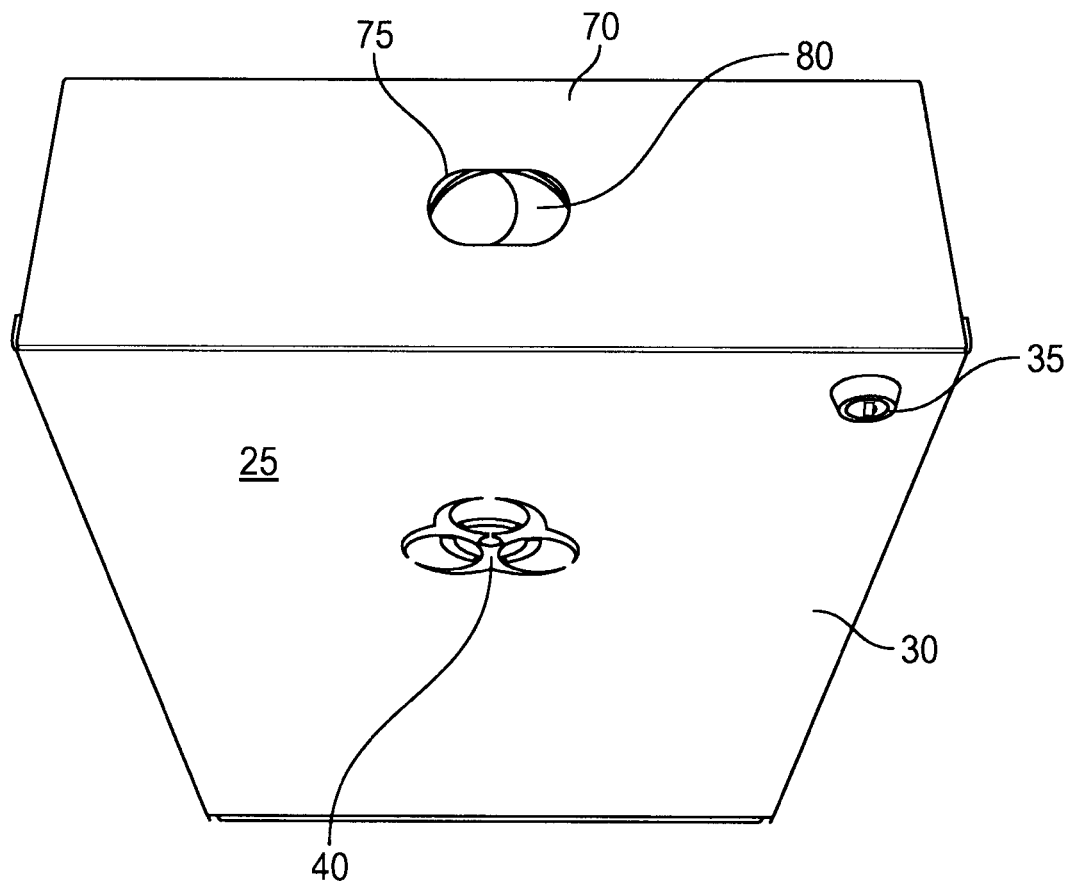
FIG. 6 is a top perspective view of the metal cabinet shown in FIG. 3.

FIG. 6 is a top perspective view of the metal cabinet 25 showing a drop tube 80 on the top panel 70. The top panel 70 has an opening 75 in the top for inserting the medical waste. Attached to the opening 75 in the top panel 70 is an inlet of the drop tube 80. The drop tube 80 transfers medical waste into the interior of the medical waste disposal container 10. For sharps disposal, the drop tube 80 is a suitable vertical drop slot for needle-down orientation of sharps waste and a preferred vertical drop technique for the safe disposal of sharps recommended by the FDA. As compared to the cabinet shown in FIG. 2, the metal cabinet 25 of FIG. 6 has a much smaller opening 75 in the top panel 70 and a drop tube 80 for eliminating the risk of waste diversion and access into the medical waste disposal container.

Figure 7:
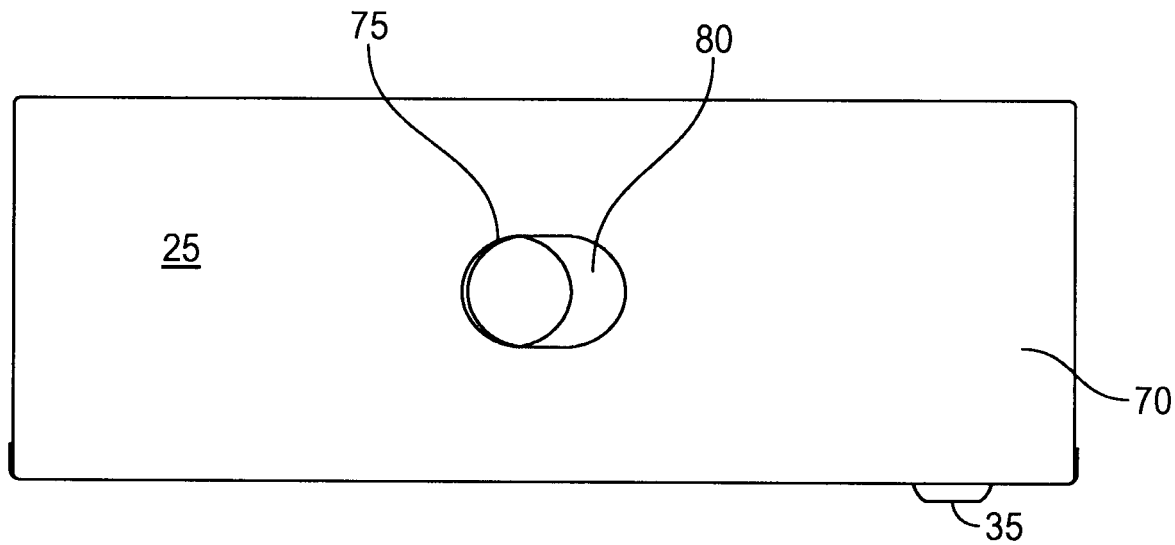
FIG. 7 is a top view of the metal cabinet shown in FIG. 3.

FIG. 7 is a top view of the top panel 70 on the medical cabinet 25. The opening 75 can be a circular opening; however, the opening 75 can be configured as other shapes. The drop tube 80 extends downward from a bottom surface of the top panel 70 into the interior of the medical cabinet 25. An outlet of the drop tube 80 is positioned just below an inlet or recessed inside an inlet of the medical waste disposal container 10. As an aspect of the drop tube 80, the drop tube 80 can be angled relative to the opening 75 in the top panel 70. The drop tube 80 can be angled between a range of 10° to 90°, 10° to 80°, 20° to 80°, 45° to 85°, or 55° to 80°, relative to the horizontal plane of the top panel 70. Additionally, the diameter of the drop tube 80 can be any suitable diameter to transfer medical waste to the medical waste container 10. As a non-limiting example, the diameter can range from 1 inch to 2 inches. The inlet of the drop tube 80 can be smaller or greater in circumference than the opening 75. As a further advantage, the angled drop tube 80 can additionally restrict an individual's fingers or hand from reaching into the medical waste disposal container 10, providing a more secure enclosure. The inlet to medical waste disposal container 10 may not always be positioned in the same position. The inlet opening to the medical waste disposal container 10 can be placed offset from the opening 75 (as shown in FIG. 8).

FIG. 8 is a front view showing the interior of the metal cabinet 25 with the front panel 30 in an opened position. In an open position, the front panel 30, side panels 45, and/or top panel 70 are movable together to open the metal cabinet 25, allowing the medical waste disposal container 10 to be inserted or removed. The drop tube 80 has a first end joined to the opening 75 and top panel 70 and a second end of the drop tube 80 is positioned within medical waste disposal container 10, such that when waste is dropped into the opening 75, the waste slides through the drop tube 80 into the medical waste disposal container 10. The drop tube 80 is preferably angled but can alternatively be configured as straight tube. The opening 75 can be positioned centrally on the top panel 70 or at any suitable location on the top panel 70.

We claim:

1. A system comprising:
a medical waste disposal container; and
a metal cabinet configured to house the medical waste disposal container; wherein the metal cabinet comprises:
 a locking mechanism for controlled access into the metal cabinet; and
 a cut-out in the metal cabinet for visualization of a portion of the medical waste disposal container; and
wherein:
a top panel of the metal cabinet defines an opening for disposal of medical waste into the medical waste disposal container;
a drop tube is positioned between the opening and an inlet of the medical waste disposal container, the drop tube angled in a range of 20 to 80 degrees relative to the opening of the top panel and configured to eliminate the risk of waste diversion and access into the medical waste disposal container; and
an outlet of the drop tube is positioned within the inlet of the medical waste disposal container.

2. The system of claim 1, wherein the locking mechanism comprises a lock/key entry, a keypad, fingerprint recognition, facial/iris recognition, a RFID tag/badge, a smart card, or any combination thereof.

3. The system of claim 1, wherein the locking mechanism further comprises an electronic system for logging information on access to the metal cabinet, wherein the information comprises date, time, individual, or any combination thereof.

4. The system of claim 1, wherein the metal cabinet comprises a stainless steel.

5. The system of claim 1, wherein the medical waste disposal container comprises a polymer.

6. The system of claim 1, wherein the medical waste disposal container further comprises a label on an exterior surface of the container.

7. The system of claim 1, wherein the cut-out is configured to allow visualization of a label on the medical waste disposal container, a barcode on a label of the medical waste disposal container, a fill line of the medical waste disposal container, a color of the medical waste disposal container, or any combination thereof.

8. The system of claim 1, wherein the medical waste disposal container is a sharps waste disposal container.

9. The system of claim 1, wherein a side vent is disposed on a side panel of the metal cabinet, and the side vent is configured to allow visualization of a color of the medical waste disposal container.

10. The system of claim 9, wherein a fill line is positioned adjacent to the side vent, the fill line indicating when to replace the medical waste disposal container.

* * * * *